US 6,537,250 B1

(12) United States Patent
Kriesel

(10) Patent No.: US 6,537,250 B1
(45) Date of Patent: Mar. 25, 2003

(54) FLUID DELIVERY DEVICE WITH ELECTRICALLY ACTIVATED ENERGY SOURCE

(75) Inventor: Marshall S. Kriesel, Saint Paul, MN (US)

(73) Assignee: Science, Incorporated, Bloomington, MN (US)

( * ) Notice: Subject to any disclaimer, the term of this patent is extended or adjusted under 35 U.S.C. 154(b) by 153 days.

(21) Appl. No.: 09/645,818

(22) Filed: Aug. 24, 2000

Related U.S. Application Data

(62) Division of application No. 09/387,447, filed on Sep. 1, 1999, now Pat. No. 6,174,300, which is a division of application No. 08/919,147, filed on Aug. 27, 1997, now Pat. No. 5,961,492.

(51) Int. Cl.[7] ........................... A61M 37/00; A61K 9/22
(52) U.S. Cl. ..................................... 604/132; 604/890.1
(58) Field of Search .................................. 604/131, 132, 604/151, 153, 185, 257, 259, 67, 90, 890.1–892.1; 128/DIG. 1

(56) References Cited

U.S. PATENT DOCUMENTS

| | | | |
|---|---|---|---|
| 5,267,980 A | 12/1993 | Dirr, Jr. et al. | 604/253 |
| 5,368,570 A | * 11/1994 | Thompson et al. | 604/132 |
| 5,403,893 A | 4/1995 | Tanaka et al. | 525/218 |
| 5,505,706 A | 4/1996 | Maus et al. | 604/131 |
| 5,721,382 A | 2/1998 | Kriesel et al. | 73/861.47 |
| 5,961,492 A | 10/1999 | Kriesel et al. | 604/132 |

* cited by examiner

Primary Examiner—Anhtuan T. Nguyen
(74) Attorney, Agent, or Firm—Schwegman, Lundberg, Woessner & Kluth, P.A.

(57) ABSTRACT

An implantable delivery apparatus for infusing medicinal fluids into a patient that includes a novel electroresponsive polymer gel material that, upon being stimulated by an electrical field, uniquely functions as an internal energy source for expelling the medicinal fields from the device.

28 Claims, 17 Drawing Sheets

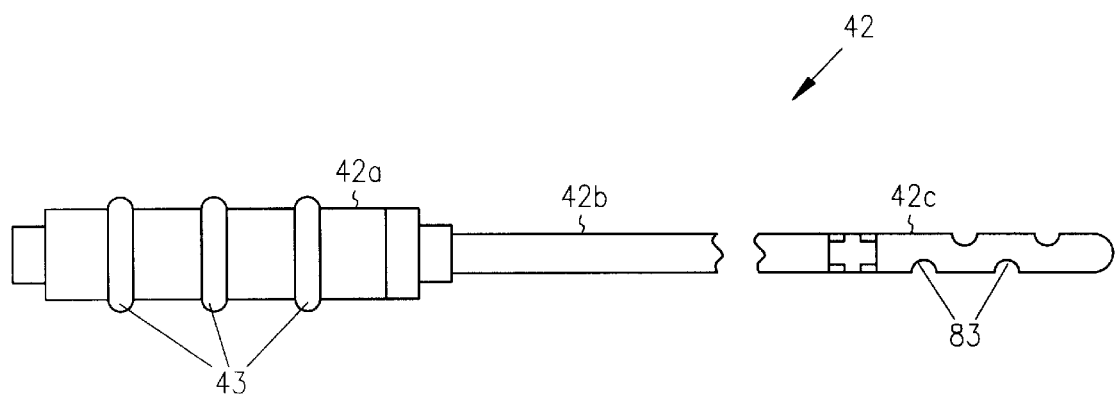
FIG. 9
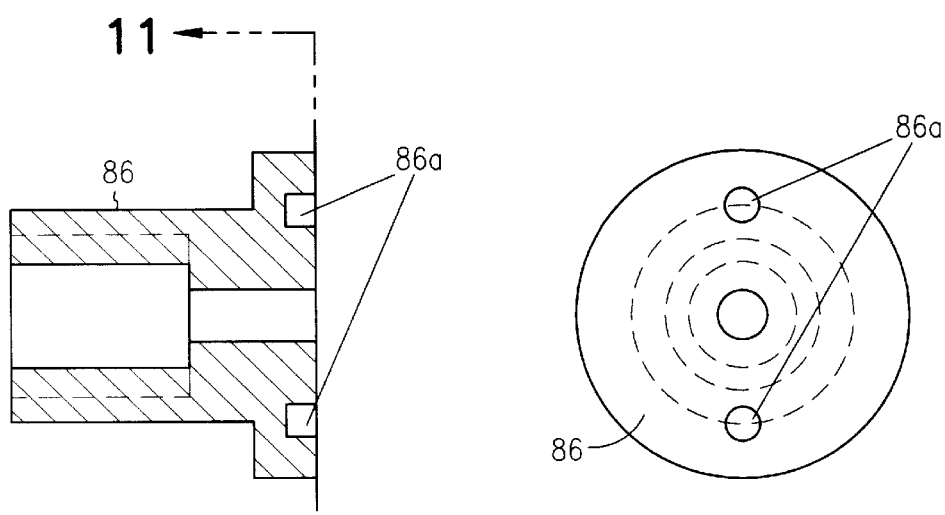
FIG. 11
FIG. 10

FLUID DELIVERY DEVICE WITH ELECTRICALLY ACTIVATED ENERGY SOURCE

This is a Continuation-In-Part of Divisional application Ser. No. 09/387,447 filed Sep. 1, 1999 now U.S. Pat. No. 6,174,300; which is a Divisional application of application Ser. No. 08/919,147 filed Aug. 27, 1997, now U.S. Pat. No. 5,961,492.

BACKGROUND OF THE INVENTION

1. Field of the Invention

The present invention relates generally to fluid delivery devices. More particularly, the invention concerns an improved apparatus having an electrically activated energy source for infusing medicinal agents into an ambulatory patient at specific rates over extended periods of time.

2. Discussion of the Invention

The oral route is the most frequent route of drug administration. Oral administration is relatively easy for most patients and rarely causes physical discomfort. However, many medicinal agents require a parenteral route of administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow means coupled with electronic based controls and typically involve the use of intravenous administration sets and the familiar bottle or solution bag suspended above the patient. Such methods are cumbersome, imprecise and, generally non-ambulatory requiring bed confinement of the patient. Periodic monitoring of the apparatus by the nurse or doctor is required to detect malfunctions of the infusion apparatus.

Devices of the character from which liquid is expelled from a relatively thick-walled bladder by internal stresses within the distended bladder have also been suggested for infusion of medicaments. For example, such bladder, or "balloon" type devices, are described in U.S. Pat. No. 3,469,578, issued to Bierman and in U.S. Pat. No. 4,318,400, issued to Perry.

A family of highly unique fluid delivery devices has been developed by the present inventor. These novel devices make use of recently developed elastomeric films, expandable foams and similar materials, which, in cooperation with a base define a fluid chamber that contains the fluid to be dispensed. The elastomeric film membrane or the expandable member controllably forces fluid within the chamber into outlet fluid flow channels provided in the device. Elastomeric film membrane devices are described in detail in U.S. Pat. No. 5,205,820 issued to the present inventor. U.S. Pat. No. 5,468,226, also issued to the present inventor, describes various types of expandable cellular elastomers and elastomeric foams used as the energy source of the fluid delivery device for expelling fluid from various physical forms of the fluid delivery device. Because of the pertinence of Pat. Nos. 5,205,820 and 5,468,226, these patents are hereby incorporated herein by reference in their entirety as though fully set forth herein. U.S. Pat. No. 5,961,492 entitled Fluid Delivery Device with Temperature Controlled Energy Source, in which the present inventor is named as a co-inventor, is also incorporated by reference as though fully set forth herein.

The apparatus of the present invention, comprises a unique implantable unit that makes use of novel electrically activated expansive material as an energy source. The apparatus of the invention can be used for the continuous infusion of a variety of beneficial agents as, for example, heparin, morphine, insulin and like agents.

SUMMARY OF THE INVENTION

It is an object of the present invention to provide a technically advanced, fluid delivery apparatus for infusing medicinal fluids into a patient that is of a compact, low profile, laminate construction. More particularly, it is an object of the invention to provide an apparatus of such a character which is implantable into the patient's body and includes a novel expanding polymer gel material which uniquely functions as an internal energy source for expelling the medicinal fluids from the device.

Another object of the invention is to provide an implantable fluid delivery apparatus that can be used for the precise infusion of various pharmaceutical fluids into the patient at controlled rates over extended periods of time.

Another object of the invention is to provide an apparatus of the forementioned character which is of a simple construction and is highly reliable in operation.

Another object of the invention is to provide an apparatus that embodies as its stored energy source, a soft, pliable, semi-solid, electroresponsive mass which is acted upon by an electrical stimulus in a manner to controllably expel fluid from the device.

Another object of the invention is to provide an apparatus as described in the preceding paragraph in which the electroresponsive mass is specifically tailored to provide precise, predictable protocol delivery of the medicinal agent stored within the reservoir of the device.

A further object of the invention is to provide a low profile, readily implantable fluid delivery device of laminate construction which can meet even the most stringent fluid delivery tolerance and flow signature requirements.

Another object of the invention is to provide a fluid delivery device of the type described that includes filling means for initial filling and subsequent refilling of the reservoir to enable continuous operation.

Another object of the invention is to provide an apparatus of the character described which is responsive to an external source of electrical stimulation, and includes a three-dimensional polymer network which functions as a stored energy source that can be constructed from various types of polymeric materials such as polyacrylamide gels.

Another object of the invention is to provide stored energy sources of the character described in the preceding paragraph which comprise blends or laminate constructions of phase transition gels that will enable the achievement of multirate delivery protocols.

Another object of the invention is to provide an apparatus of the character described which includes a novel, combination filter and rate control assemblage disposed intermediate the fluid reservoir and the outlet port of the device or intermediate outlet port of the device and the infusion means.

Another object of the invention is to provide an implantable device having an expandable gel which functions as an internal energy source that includes sensor means for sensing physiological changes in the patient's body.

Another object of the invention is to provide an apparatus of the character described which, due to its unique construction, can be manufactured inexpensively in large volume by automated machinery.

Other objects of the invention will become apparent from the discussion which follows.

BRIEF DESCRIPTION OF THE DRAWINGS

FIG. 9 is a top plan view of the cannula assembly of the apparatus shown in FIG. 1.

FIG. 10 is a cross-sectional view of the cannula closure member that secures the cannula assembly in position relative to the outlet port of the apparatus.

FIG. 11 is a view taken along lines 11—11 of FIG. 10.

DESCRIPTION OF THE INVENTION

Figure 1:
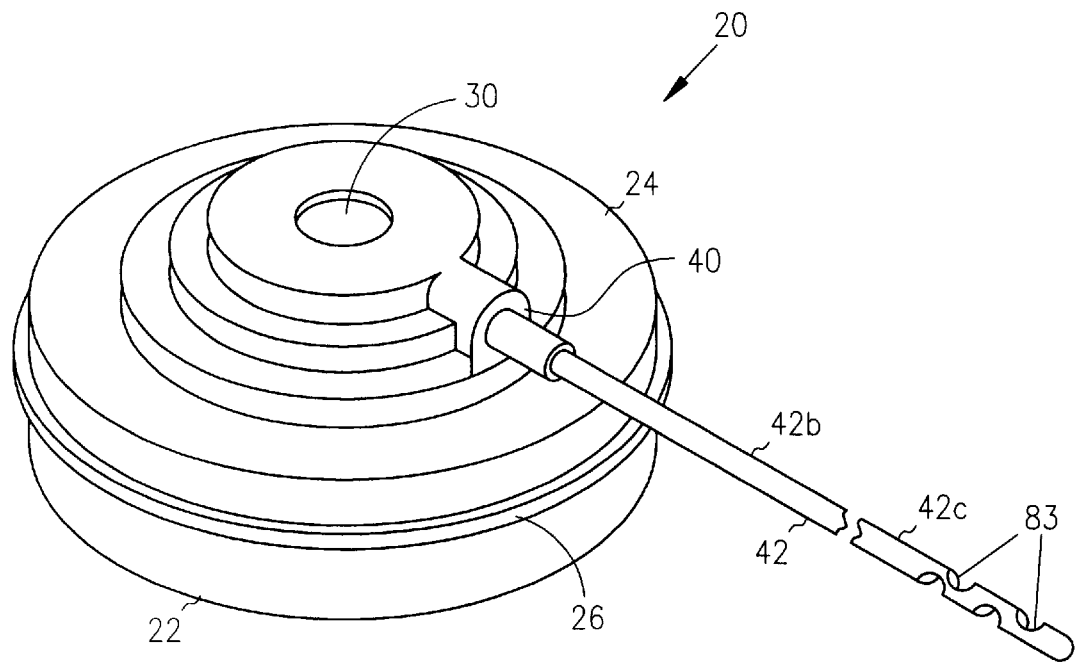
FIG. 1 is a generally perspective view of one form of implantable medicament delivery device of the invention.
Figure 2:
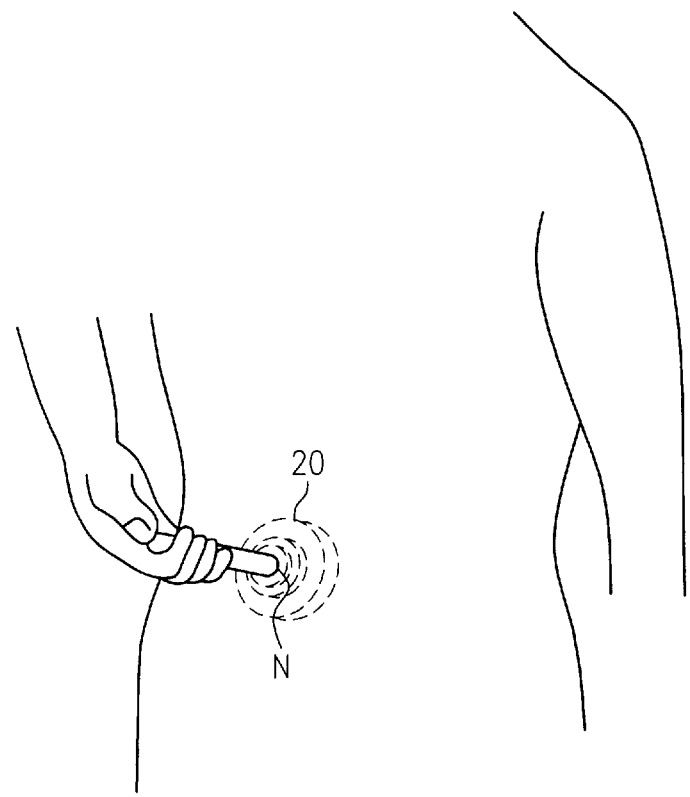
FIG. 2 is a generally perspective, illustrative view showing the delivery device of FIG. 1 implanted within the patient's body and illustrating the filling of the reservoir of the device using a conventional, external hypodermic syringe
Figure 3:
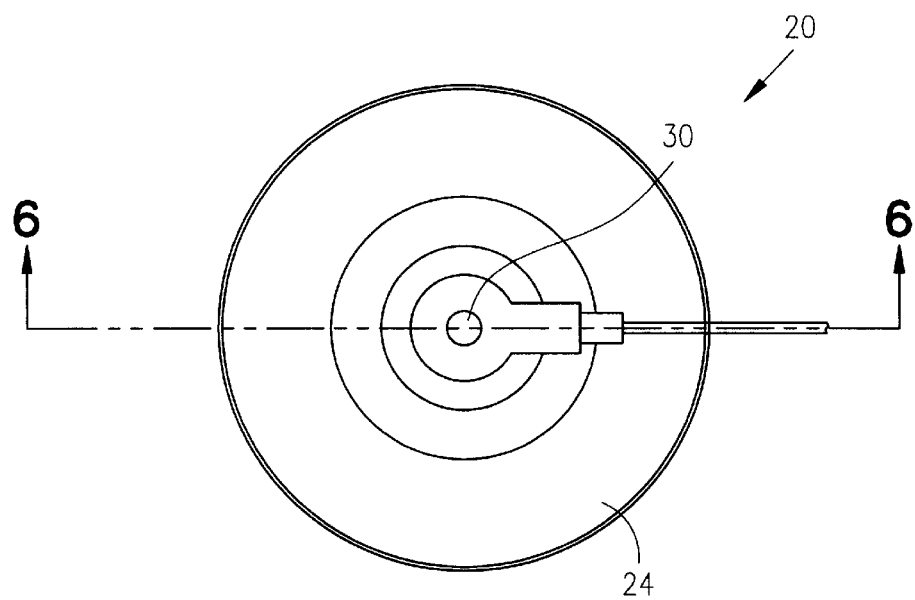
FIG. 3 is a top plan view of the fluid delivery apparatus of the invention shown in FIG. 1.
Figure 4:
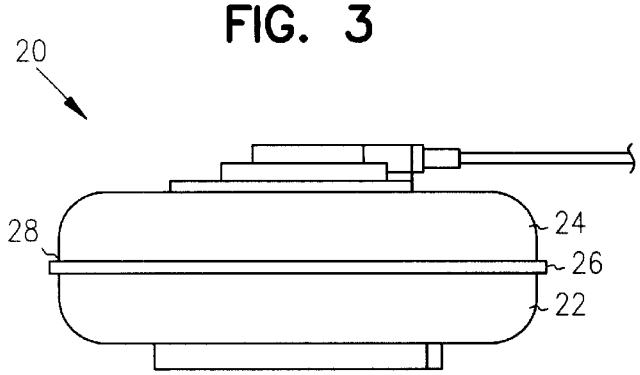
FIG. 4 is a side view of the device shown in FIG. 3.

Referring to the drawings and particularly to FIGS. 1 through 18, one form of the apparatus of the invention is there shown and generally designated by the numeral 20. As indicated in FIG. 2 of the drawings, this embodiment of the invention, is specially designed to be implanted into the body of the patient. As shown in FIGS. 1 through 8, the apparatus here comprises a titanium base or shell 22 and a titanium cover or shell 24 that can be joined together as by welding at interface 26 to form the hollow, hermetically sealed housing 28 of the device.

Figure 6:
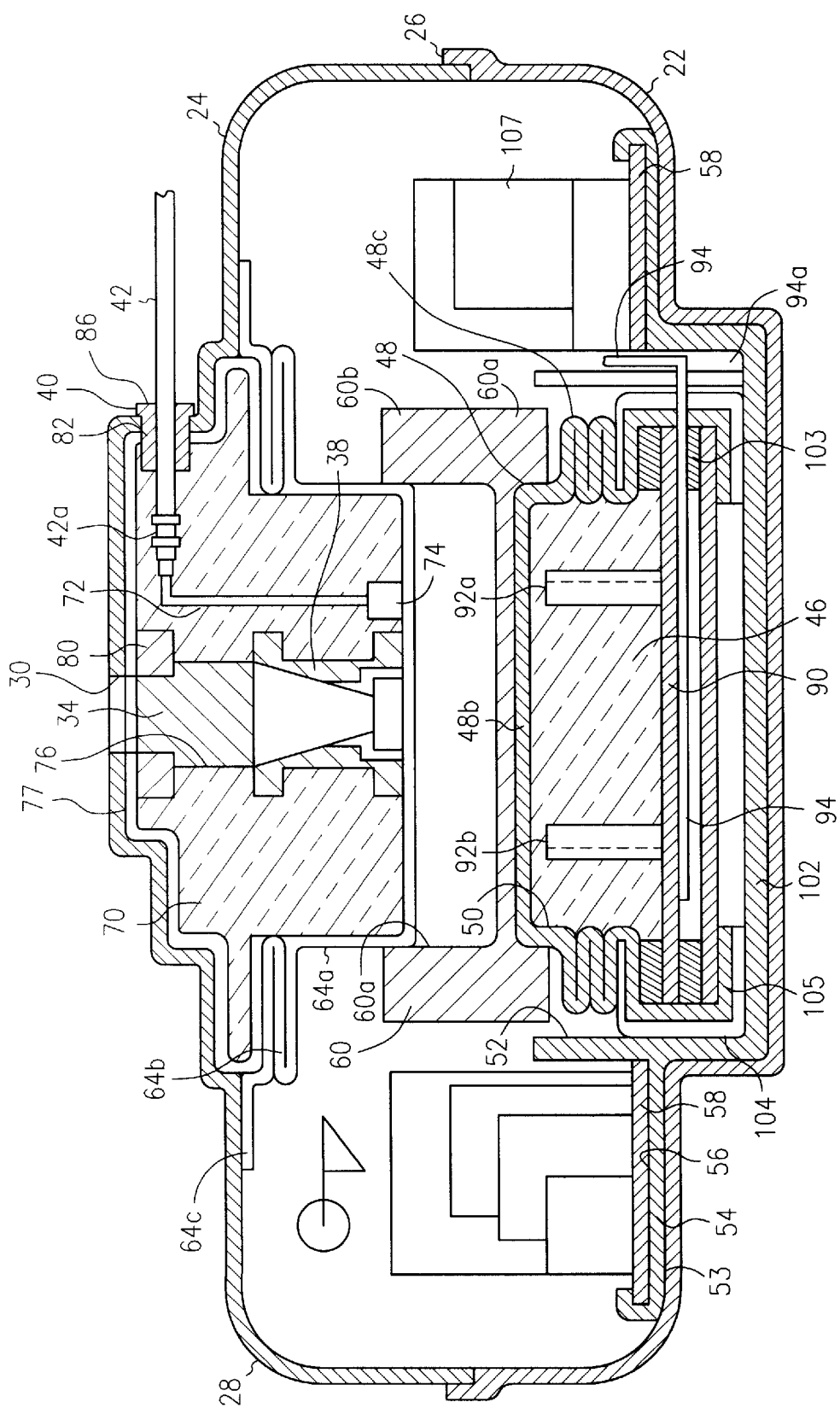
FIG. 6 is an enlarged cross-sectional view taken along lines 6—6 of FIG. 3 showing the reservoir empty.
Figure 7:
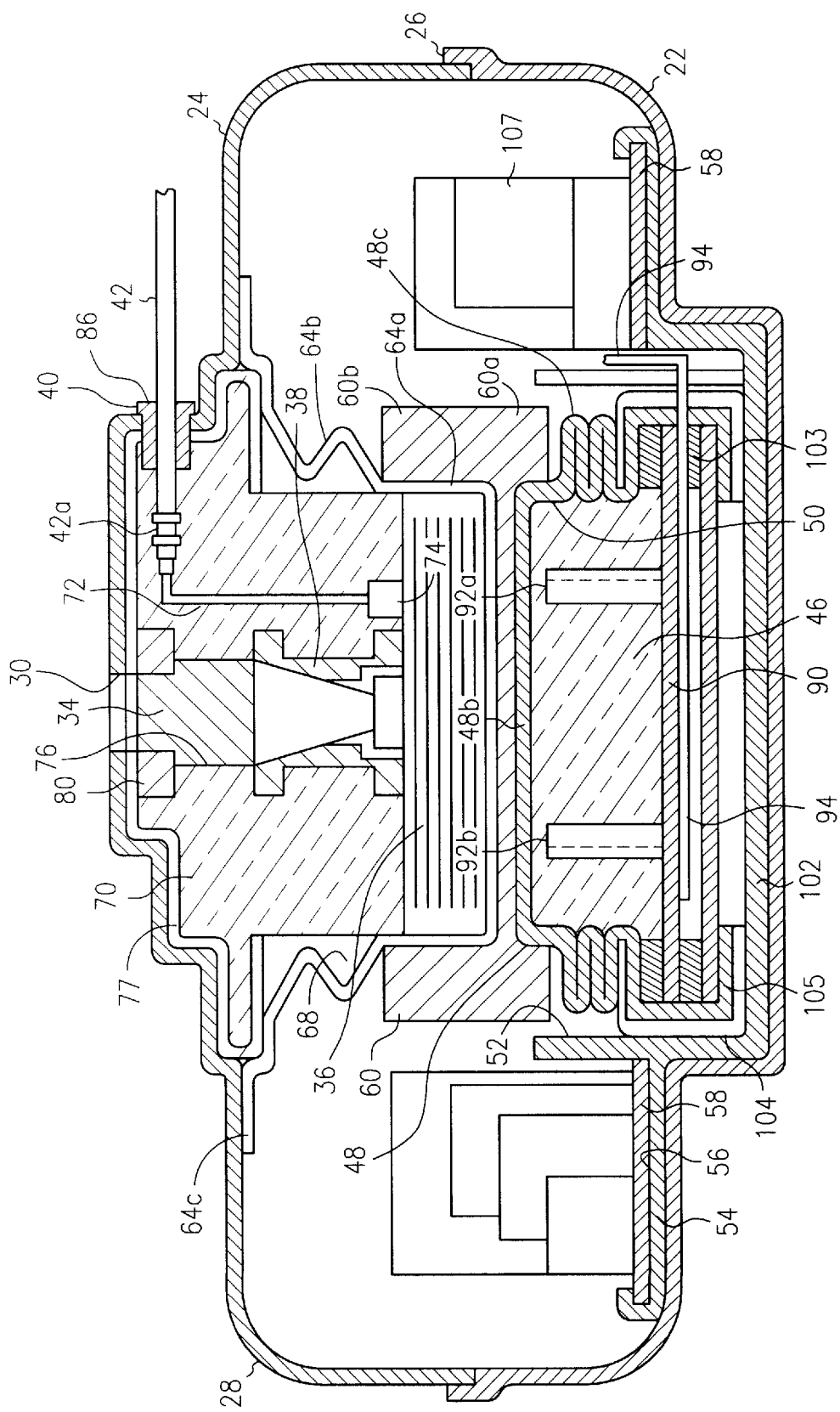
FIG. 7 is a cross-sectional view similar to FIG. 6, but showing the reservoir in a filled condition.

Preferably the device is adapted to be implanted within the patient's body at a location immediately below a layer of skin and includes fill means for filling the device reservoir. The fill means here comprises an access port 30 formed in cover 24 that can be accessed by a hypodermic needle "N". With the arrangement shown in FIGS. 1 and 2, the hypodermic needle can be inserted through the skin to introduce, via the access port, a quantity of liquid medicament such as heparin, morphine, insulin or like medicament through a septum 34, which also forms a part of the fill means, into a medicament reservoir 36. A tapered needle guide 38 disposed within the ullage means of the device supports septum 34 and guides the entry of the hypodermic needle toward reservoir 36 (FIGS. 6 and 7).

Figure 8:
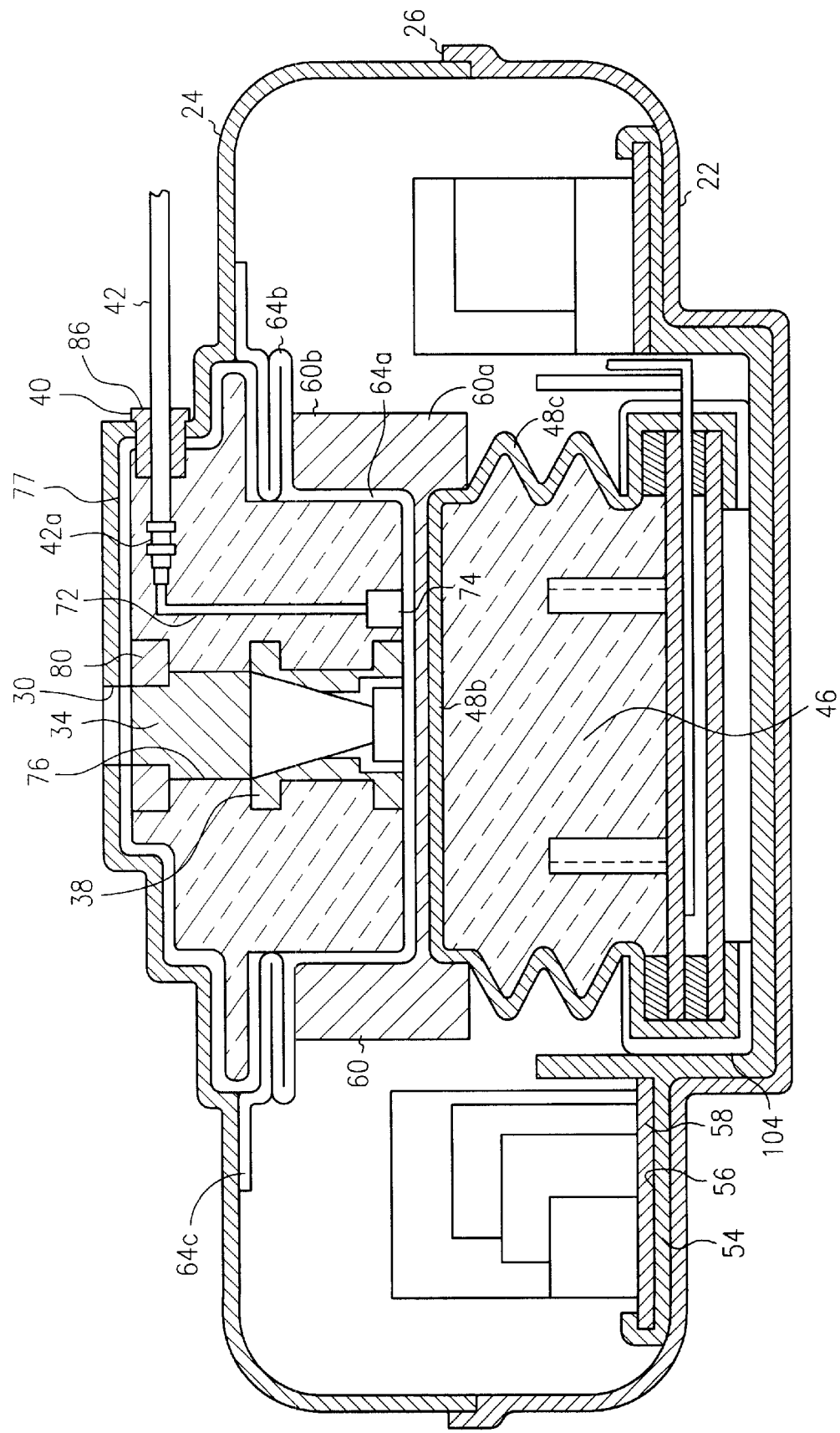
FIG. 8 is a cross-sectional view similar to FIG. 7, but showing the expandable gel in an expanded configuration following delivery of substantially all of the medicament to the patient.

During operation, the medicament is delivered from the delivery device via a cannula port 40 to which a delivery means for delivering fluid to the patient is attached. The delivery means here comprises a cannula assembly 42 (FIGS. 1 and 8). Cannula assembly 42 is strategically positioned at the time of implant to deliver the medicament to a selected therapeutic site within the patient's body by means of a suitable porous tip cannula, the character of which will presently be described.

Housing 28 houses the novel electrically activated stored energy source of the invention which functions to cause the fluids contained within the sealed reservoir 36 (FIG. 7) of the device, the character of which will presently be described, to flow outwardly thereof through cannula assembly 42. The stored energy source is provided in the form of an electroresponsive expandable polymer mass 46 which is disposed within an expandable, hermetically sealed structure or metal bellows assembly 48 that is mounted within housing 28 in the manner best seen in FIGS. 6,7, and 8. In some instances, expandable mass 46 comprises a laminate construction made up of various gel compositions that can be operably associated with one another to perform mechanical work. Alternatively, expandable mass 46 can comprise a single gel such as, for example, a polyacrylamide gel having certain novel attributes which will presently be described.

Figure 12:
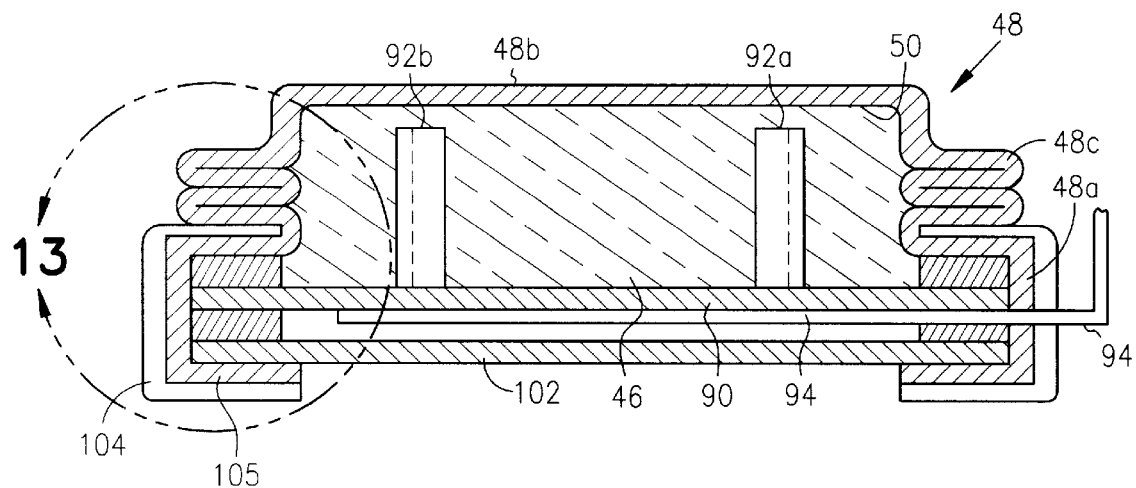
FIG. 12 is a cross-sectional view of the bellows assembly that houses the expandable gel of the apparatus.
Figure 13:
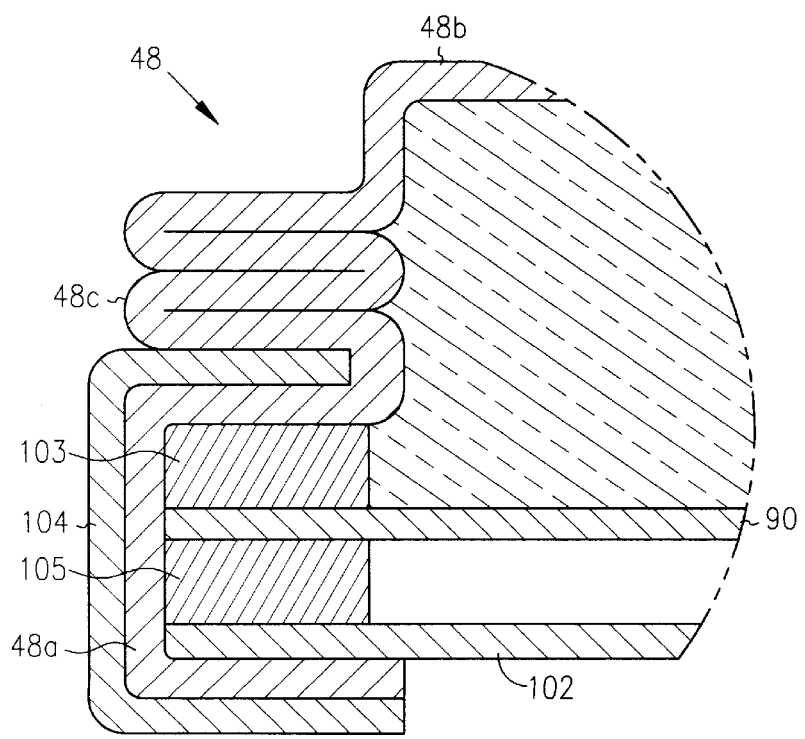
FIG. 13 is an enlarged, fragmentary, cross-sectional view of the area designated as 13 in FIG. 12.

As best seen in FIGS. 12 and 13, bellows assembly 48 includes a base portion 48a, an upstanding, reduced diameter cover 48b and an expandable bellows-like sidewall 48c which are interconnected to define the gel receiving chamber 50. Bellows assembly 48 is closely received within a receiving chamber 52 formed in a carrier assembly 54, which is, in turn, received within base 22.

As illustrated in FIGS. 6 and 7, surrounding chamber 52 is an electronics receiving channel 56 that supports an annular shaped, printed circuit (PC) board 58 and the electronic components 107 associated therewith, the character of which will presently be described. Upstanding cover 48b of bellows assembly 48 is closely received within the lower portion 60a of a generally annular shaped capture ring 60 (FIGS. 6 and 15) that is disposed intermediate base 22 and cover 24 of housing 28.

As best seen in FIG. 7, the base portion 64a of an expandable bellows structure, which forms the upper reservoir assembly 64 of the apparatus is receivable within the upper portion 60b of the capture ring 60. Reservoir assembly 64 is operably associated with bellows assembly 48 in the manner shown in FIGS. 7 and 8. Connected to base portion 64a is a bellows-like wall 64b, which cooperates with base portion 64a to form the expandable fluid reservoir 36 of the apparatus (FIG. 7). Connected to wall 64b is a connector flange 64c that can be sealably interconnected with the lower surface of cover 24, as by welding, to form a hermetically sealed chamber 68, a portion of which comprises medicament reservoir 36 (see FIGS. 7 and 16).

Figure 16:
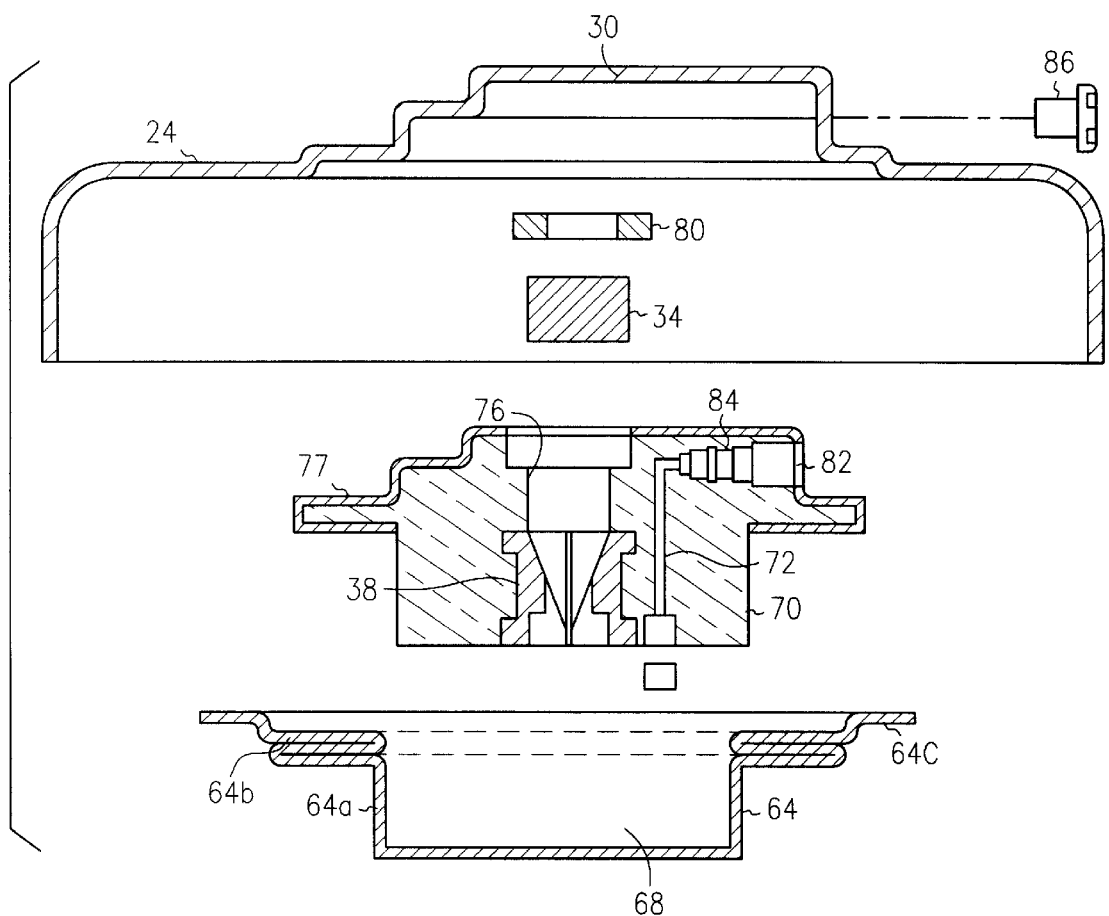
FIG. 16 is an exploded, cross-sectional view of the upper half shell of the apparatus that houses the upper reservoir bellows, the ullage and the fill septum assembly.

Disposed within chamber 68 is a novel co-molded plastic ullage assembly 70 which includes a fluid passageway 72 that is in communication with reservoir 36 via an impedance frit 74 and with cannula port 40. Formed within ullage assembly 70 proximate needle guide 38 is a septum receiving chamber 76 that houses septum 34 that is pierceable by the needle "N" of the hypodermic syringe used to fill reservoir 36. Ullage 70 is partially encapsulated within an elastomer 77. Septum 34 is accessible through a sealing ring 80 that is disposed proximate cover 24 (FIG. 16). Also formed within ullage assembly 70 is an internally threaded cannula connector portion 82 to which the delivery cannula assembly 42 of the apparatus can be sealably interconnected (FIGS. 6, 10 and 11). As best seen by referring to FIG. 9, cannula assembly 42 comprises an elastomeric molded connector portion 42a that is provided with a plurality of spaced apart, riblike protuberances 43. Connected to connector portion 42a is a hollow cannula 42b that includes a porous tip 42c that permits fluid to flow outwardly through small outlet passageways 83 formed in the porous tip 42c. Connector portion 42a is sealably receivable within the internally ribbed connector port 84 (FIG. 16). As best seen in FIG. 6, a threaded cannula closure member 86 (FIGS. 10, 11 and 16), which is threadably receivable within the threaded connector port 82 formed in ullage 70 functions to hold the cannula assembly in position and to compress connector portion 42a in a manner to insure maintenance of a leak-tight seal between the cannula assembly and the device housing. An appropriate spanner wrench (not shown) can be used to engage apertures 86a (FIG. 11) to threadably interconnect member 86 with ullage 70.

Figure 14:
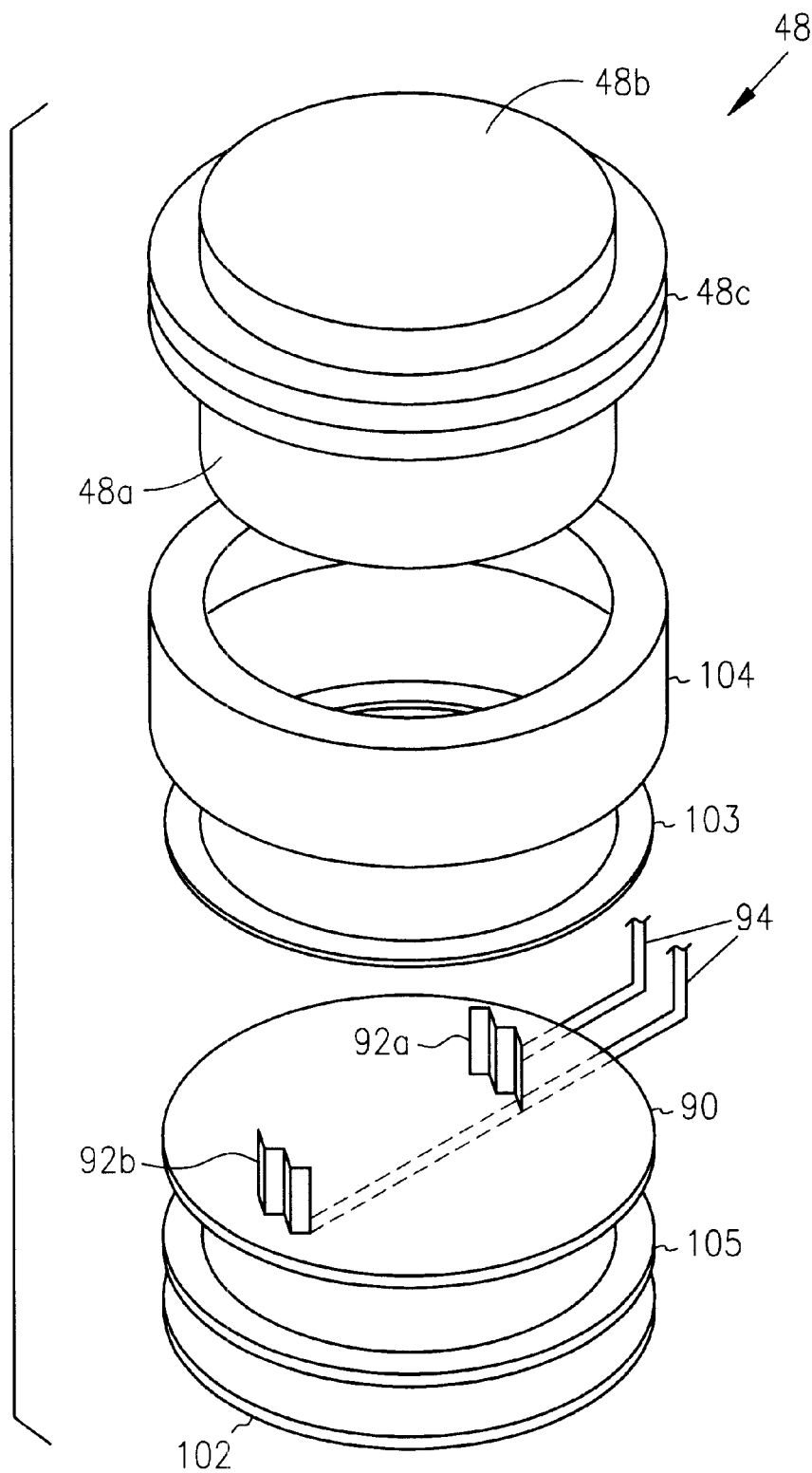
FIG. 14 is a generally perspective, exploded view of the assembly shown in FIG. 12.
Figure 15:
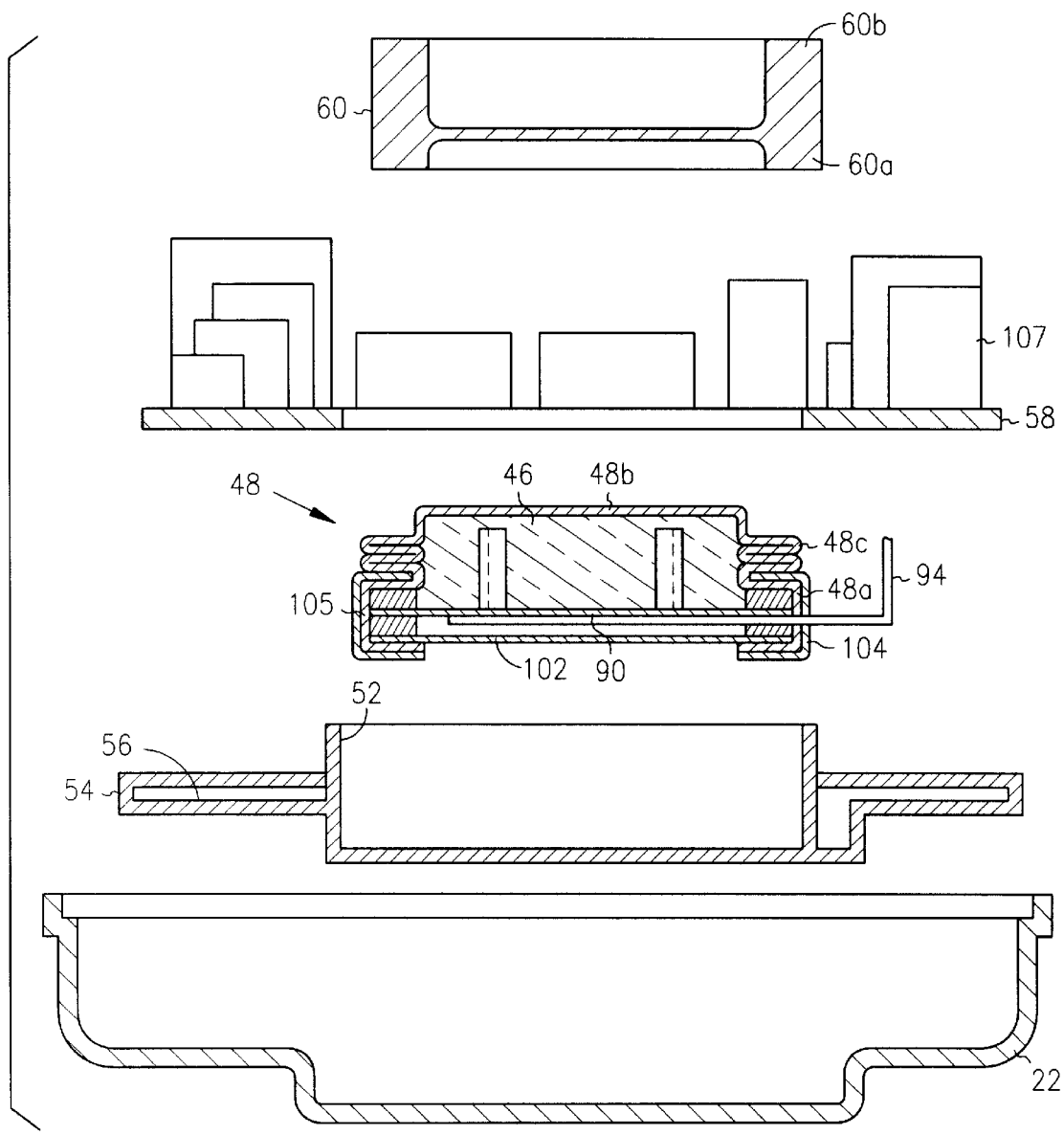
FIG. 15 is an exploded, cross-sectional view of the lower half shell of the apparatus that houses the carrier assembly, the connector ring, the bellows assembly, the expandable gel, the electric circuit and the electronics associated therewith.

Considering next the activating means of the invention for activating the expandable mass or gel 46, this novel means here comprises a source of electric current that includes a generally circular shaped base 90 and first and second upstanding electrodes 92a and 92b that are connected to base 90 in the manner best seen in FIG. 14. Electrodes 92a and 92b can be constructed from various materials including platinum and one electrode is positively charged while the other is negatively charged so as to create an electrical field therebetween and across gel 46. Electrodes 92a and 92b are interconnected with a source of electrical power such as battery 116 via the circuit interface of a control system by a pair of wire leads 94 (FIGS. 14 and 18) that are potted in place using a conventional potting compound 94a (FIG. 6). As best seen in FIGS. 12, 13 and 14, base 90 is supported by a closure plate 102 that is connected to base 48a of bellows 48, as by welding, so as to hermetically sealably encapsulate the electrodes in the manner shown in FIG. 12. Positioned between base 90 and portion 48c of the bellows assembly is a spacer ring 103. Another spacer ring 105 is positioned between base 90 and plate 102 to permit the passage of wire leads 94 into the housing. A bellows clamp ring 104 circumscribes the lower portion of the bellows assembly in the manner indicated in FIGS. 12 and 13.

By way of example, power can be supplied to electrodes 92a and 92b either continuously or intermittently. When power is continuously supplied to electrodes 92a and 92b, an electrical field will generated between the electrodes. When power is interrupted, thereby changing the electric field, certain types of electroresponsive gels will swell. In contradistinction, when certain other electroresponsive gels are used, the act of supplying power to the electrodes will create an electrical field that will act upon the electroresponsive gel so as to cause an appropriate swelling thereof. This phenomenon will be discussed further hereinafter. In any event, the characteristics of the expandable gels can be used to drive the cooperating bellows to cause a controlled expelling of the fluid from reservoir 36.

Considering now, in greater detail, the novel expandable mass or gel 46, like most gels, gel or mass 46 is of a semisolid form that can advantageously be handled without external containment under ambient manufacturing conditions. From a technical viewpoint, gels are often characterized as soft solids which reside in a state between a liquid and a solid state. Frequently gels comprise a cross-linked network of long polymer molecules with liquid molecules trapped within the network. Many gels known in the prior art not only are capable of significantly large volume change in response to stimulus (phase-transition gels), but also exhibit physical characteristics that enable them to closely conform to the shape of an adjacent member such as a distendable member.

Phase transition gels best suited for use in constructing the electroresponsive expandable mass of the present invention are gels which undergo a change in polymer conformation and in so doing exhibit a large volume change at a given phase-transition condition. Unlike liquids, which exhibit a fixed temperature for state of vaporization to a known volume and with such vaporization point changing as a function of ambient pressure, the phase-transition gels in this invention are multicomponent polymers which can be made to respond with various volume changes to a singular external stimuli to perform useful work.

Advantageously, the difference in volume between the expanded phase of these phase-transition gels and the contracted phase thereof can be orders of magnitude. Examples of a number of different types of phase-transition gels are disclosed in Tanaka et al., U.S. Pat. No. 4,732,930; No. Re-35068 and U.S. Pat. No. 5,403,893. Because of the pertinence of these patents, U.S. Pat. Nos. 4,732,930, 5,403,893 and Pat. No. Re-35068 are all hereby incorporated by reference as though fully set forth herein.

The responsive gels may also be reversibly responsive. For example, when such gels experience certain environmental changes, the entire gel, or a component thereof will undergo a reversible volumetric change which typically involves a shift between two equilibrium states as, for example, expanded and collapsed. This reversible volume change of the entire gel, or a component of the gel may be either continuous or discontinuous. Typically, a continuous volume change is marked by a reversible change in volume that occurs over a substantial change in environmental condition. On the other hand, the gel, or a component thereof, may undergo a discontinuous volume change in which the reversible transition from expanded to collapsed states, and back again, typically occurs over a relatively small change in environmental condition. A gel undergoing a continuous phase-transition may have a similar order of magnitude total volume change as a gel undergoing a discontinuous phase-transition.

Typically, volumetric changes in the phase transition gels result from competition between intermolecular forces, usually electrostatic in nature. Such volumetric changes are believed to be driven primarily by four fundamental forces, that is ionic, hydrophobic, hydrogen bonding and van der Waals bonding interactions, either alone or in combination.

Gels suitable for use as the stored energy sources of the present invention include the many polymer gel systems that respond to electrical stimuli. In this regard, it is has long been recognized that such gels swell, shrink and bend in the presence of an electric field (Shiga, T. Proc. *Japan Acad. Ser. B* 1998, 74,6; Osada Y. J. *Macromol. Sci. Chem.* 1991, 11–12, 1189; Shinohara, S. J. *Intel. Mater. Syst. Struc.* 1996, 7, 254; Tanaka, T. *Science* 1982, 218, 469; Sansinena, J *M. Chem. Commun.* 1997, 2217; Osada, Y. J. *Biomater. Sci. Polymer Edn,* 1994, 5,485). The response of an electroresponsive gel to an electrical current depends largely on the chemical constituents that make up the gel, the chemical species used to carry the applied current and the associated hardware (e.g. the electrodes).

One classic example of a gel that responds to an electrical stimulus is given by Tanaka et al. (Tanaka, T. *Science* 1982, 218, 469). In particular, polyacrylamide gels that contained 20% acrylic acid groups were employed. In water, these gels were partially ionized and hence capable of responding to an electrostatic force from an electrode. When the gel was placed between two platinium electrodes and a current was applied, the gel was pulled toward the positive electrode. At applied voltages>1.25 V, the gel collapses greater than 200-fold in volume due to a uniaxial stress along the gel axis. When the applied electric field was removed, the gel returned to its original swollen state. In principle, analogous collapsible gels could be made by modifying most polymeric gels such that they contain ionizable carboxylate groups. For example, any polyacrylamide gel could be partially hydrolyzed (in the presence of acid or base) to yield a species that is ionized in water. Alternatively, most synthetic polymers that are capable of forming gels could have carboxylate groups incorporated into the polymeric backbone. This could be accomplished in the initial synthesis of the polymer chains or via cross-linking reactions. Additionally, other anionic functional groups introduced into the gel network should cause a swollen gel structure to collapse in the presence of an electric field. For example, a polymer gel containing sulfonate (rather than carboxylate) groups should respond to an electric field in an analogous way as Tanaka's system previously described. Polysulfonate gels have been described previously by Shirahama et al. (Colloids Surf., A 1996, 112, 233). A typical poly (acrylamidosulfonic acid) gel prepared by standard cross linking of, for example 2-acrylamido-2-methylpropanesulfonic acid and N,N'-methylenebis- acrylamide, could also be deprotonated using an alkali solution to yield a polysulfonate gel containing a definite charge. Another suitable gel for this device is hyaluronic acid hydrogel. This material is a naturally occurring polysaccharide containing ionizable carboxylate groups. In the presence of an electric field of 5 V/cm, this gel loses two-thirds of its volume in 30 min. (Florence, A. T. *J Controlled Release* 1995, 33, 405). Other researchers have also observed the collapse of polyacrylic acid gel beads in the presence of an electric field (Osada, J. *Macromol. Sci. Chem.* 1991, 11 & 12, 1189). In these materials, the collapse of the gel was attributed to an electrokinetic phenomenon. That is, the water and ions in the gel migrate toward the electrode bearing the opposite charge to that of the gel. Further it is important to note, that an applied electric field does not induce contraction of neutral hydrogels, i.e. those that do not contain ionized functional groups (Osada, J. *Macromol. Sci. Chem.* 1991, 11 & 12, 1189). Polyacrylonitrile gel fibers have also been reported as electrically responsive materials.

In light of these teachings, a gel that collapses in response to an applied electric field can be reliably used in the devices of the present invention. It should also be noted that by using other gels, or laminate gel constructions, the applied electric field can be started at some relatively high voltage and then decrease at a controlled rate. Under these conditions, the gel will slowly expand and the drug fluid will accordingly be expelled in a correspondingly controlled fashion.

Figure 5:
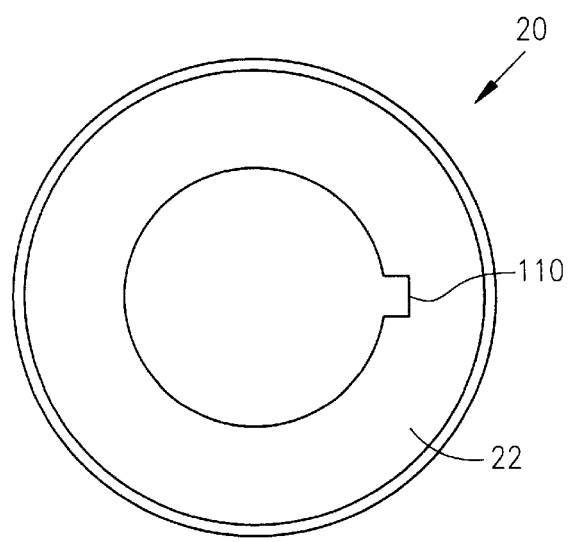
FIG. 5 is a bottom view of the device shown in FIG. 4.
Figure 17:
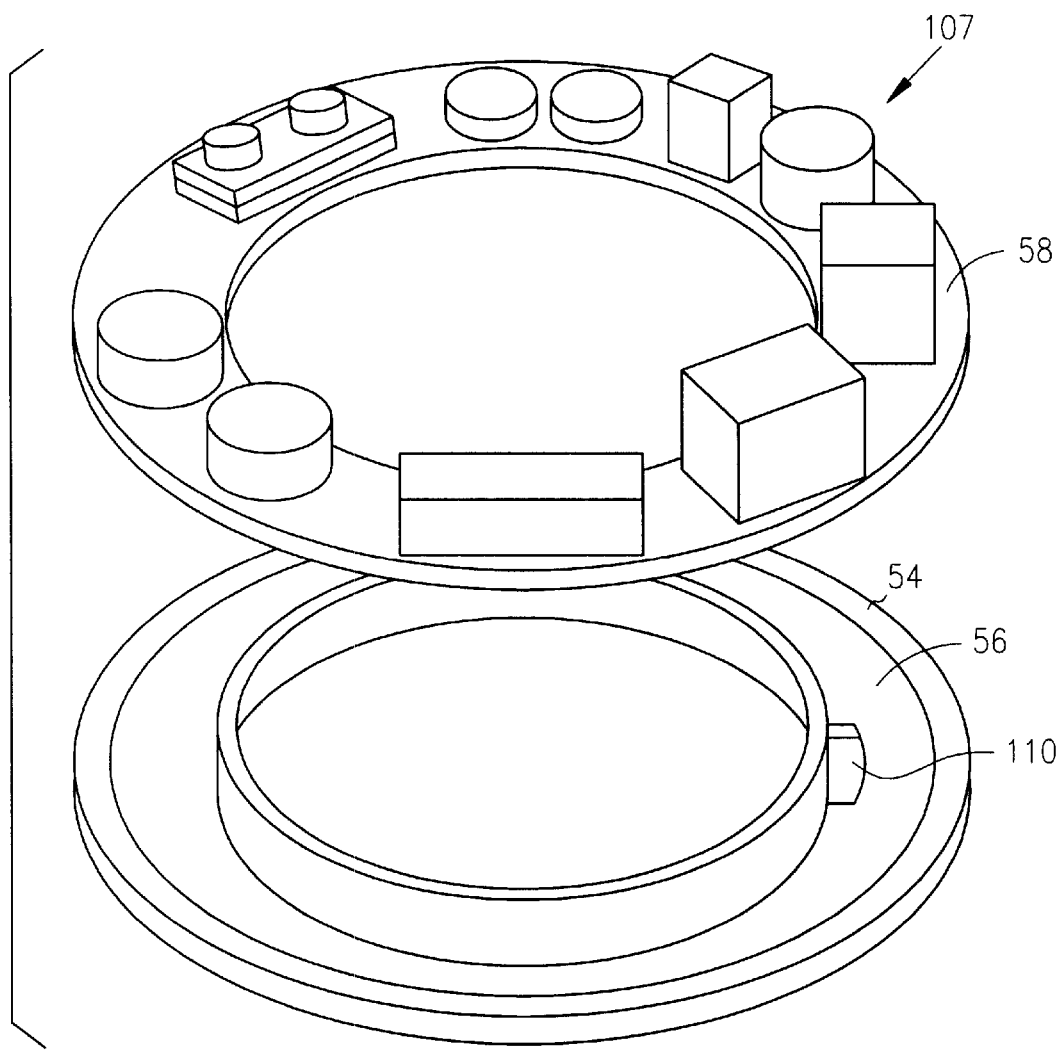
FIG. 17 is a generally perspective, exploded view of the carrier assembly, the printed circuit board and the associated electronics of the apparatus.

In using the apparatus of the invention, either before or after the reservoir has been filled in the manner shown in FIG. 7, the electronic controller can be programmed. The electronic controller here includes a mircoprocessor, a RAM/ROM memory, a power supply, feed back electronics, amplifiers circuits, timing and control switch matrix circuits and various related circuitry (see FIG. 18). In a manner presently to be described in greater detail, the controller can be programmed to enable the precise delivery of varying dosing volumes over time in response to a programmed delivery protocol. The electronic controller can also be programmed to indicate function status to the user. The wiring leading to the electronics 107 is introduced through the electronic lead cavity 110 formed in base 22 (FIGS. 5 and 17).

Figure 18:
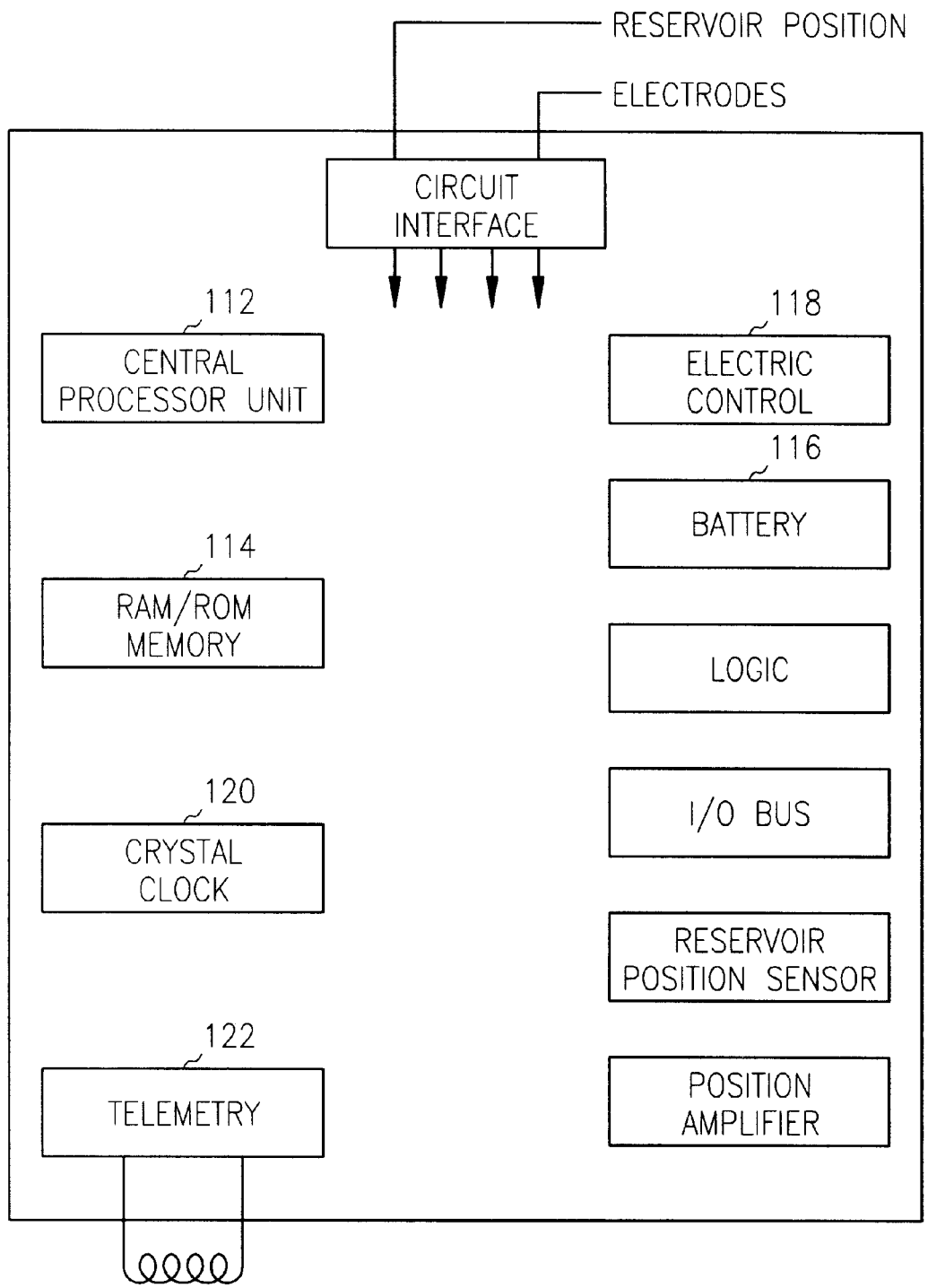
FIG. 18 is a generally diagrammatic view showing the relationship among the various components of the central control unit and stimulation means of the embodiment shown in FIG. 1.
Figure 19:
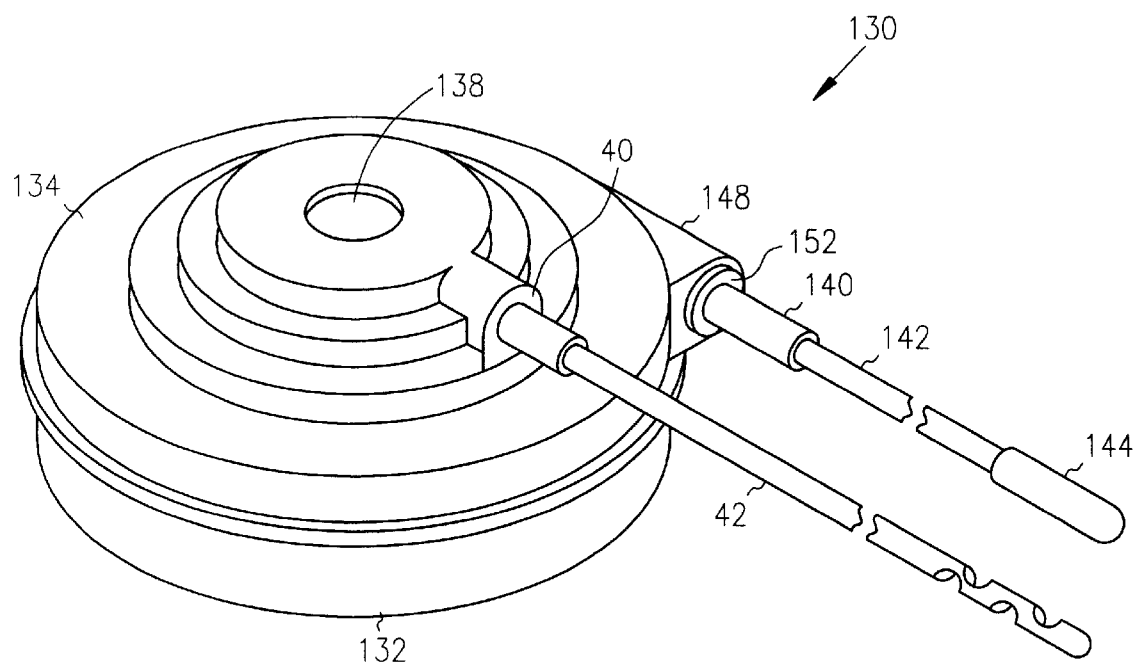
FIG. 19 is a generally perspective view of yet another form of the fluid delivery apparatus of the invention that is implantable within the patient's body.
Figure 20:
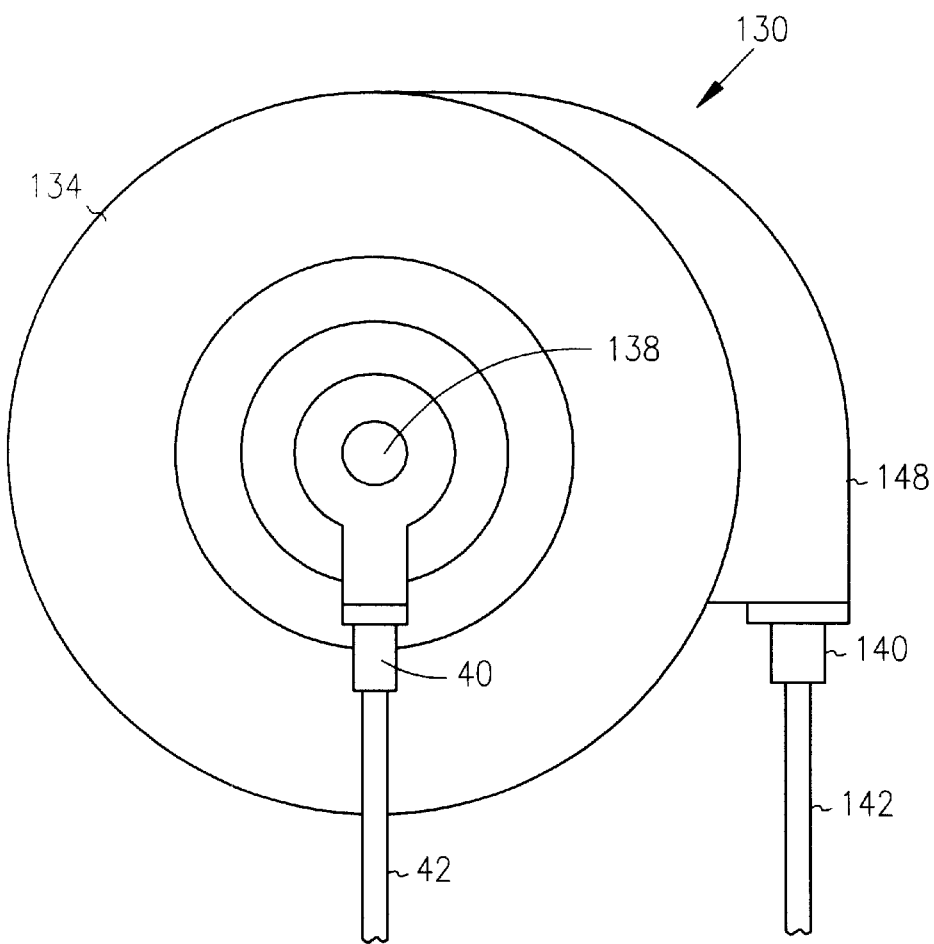
FIG. 20 is a top plan view of the apparatus shown in FIG. 19.
Figure 21:
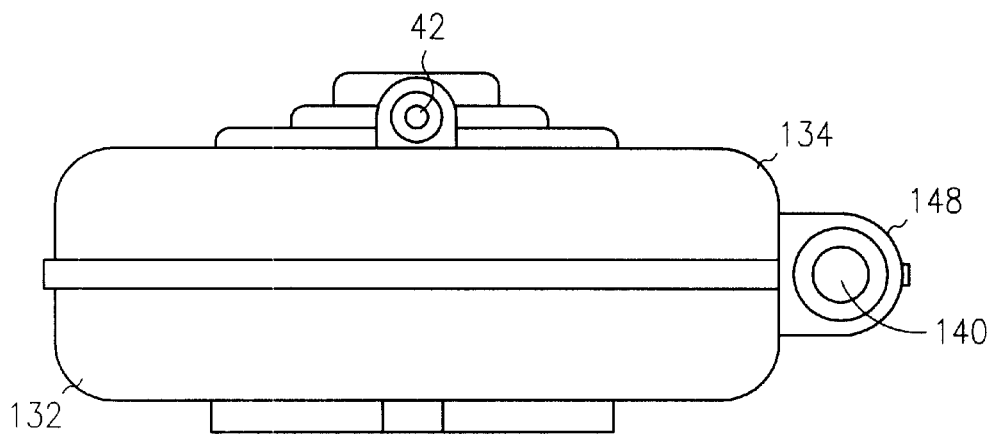
FIG. 21 is a side-elevational view of the apparatus shown in FIG. 20.
Figure 22:
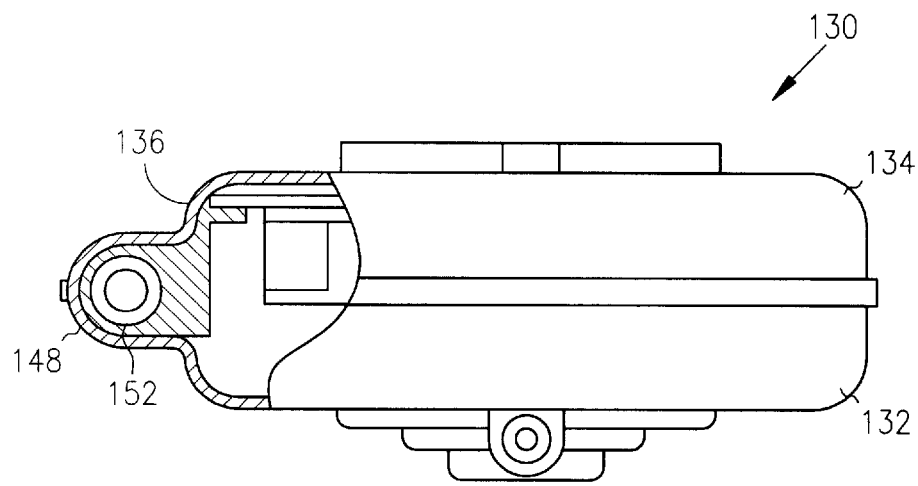
FIG. 22 is a side-elevational view of the apparatus partly broken away to show internal construction.
Figure 23:
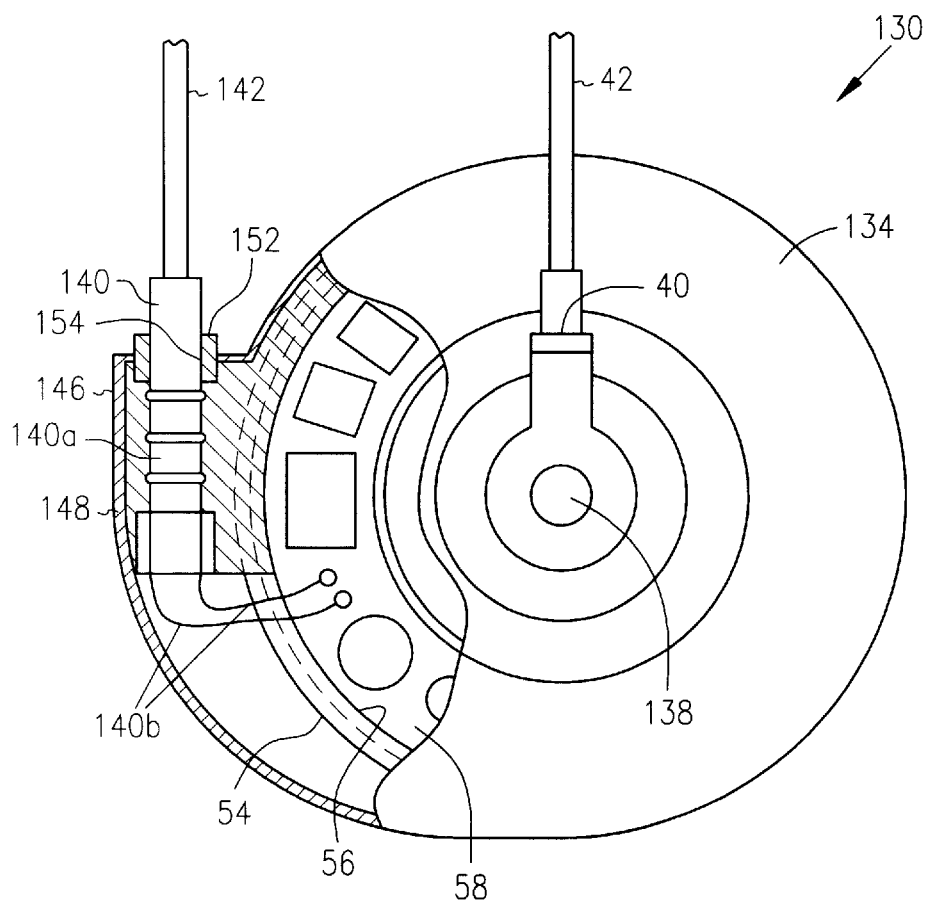
FIG. 23 is a top plan view of the apparatus partly broken away to show internal construction.
Figure 25:
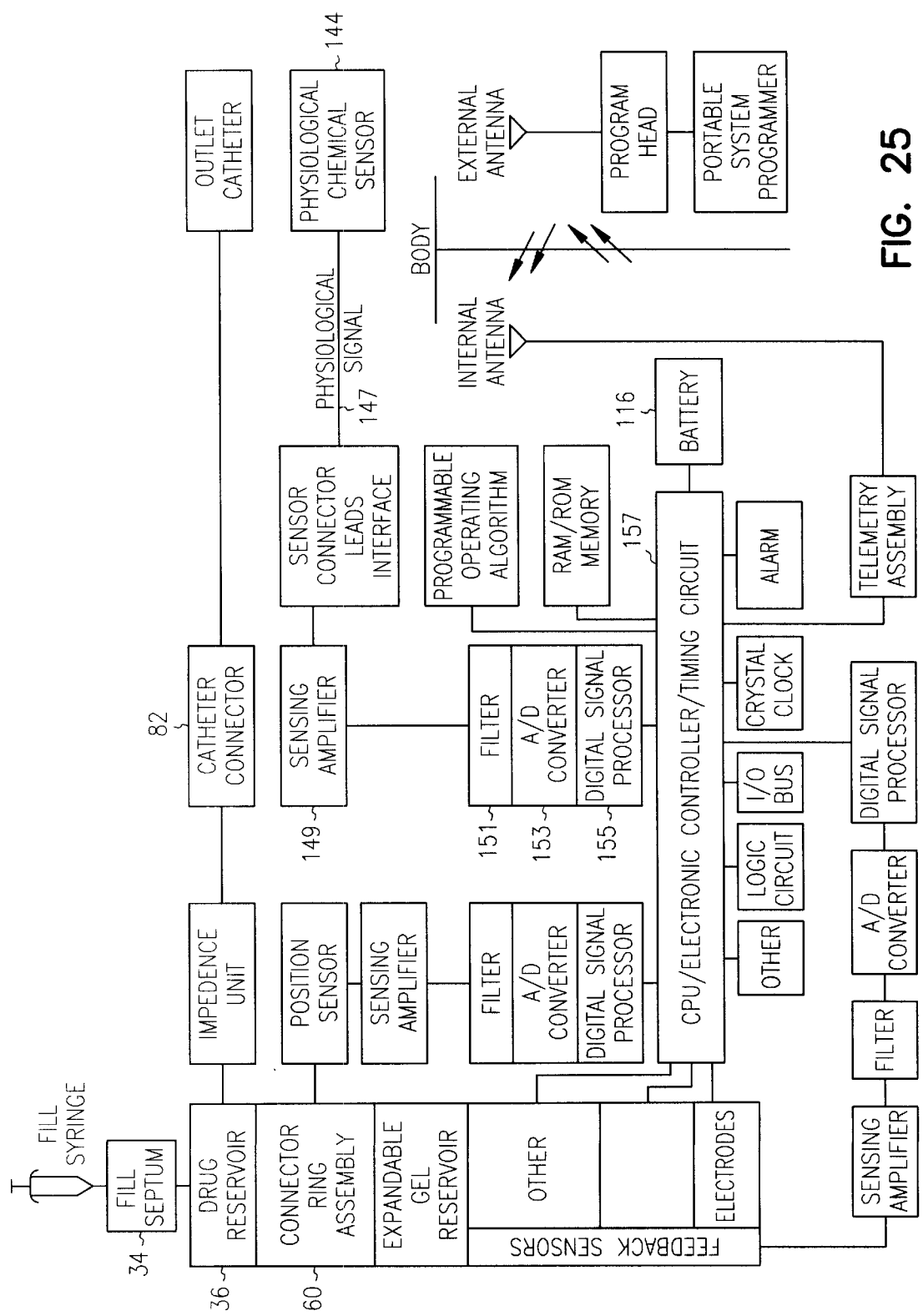
FIG. 25 is a generally diagrammatic view further illustrating the relationship among the major operating components of the apparatus including an implantable physiological sensor, system telemetry and external programming capability.

As shown in FIG. 18, the electronic controller comprises a central processing unit 112 having a memory 114 and a conventional power source such as a commercially available magnesium oxide or lithium battery 116 (FIG. 25). Also forming a part of the electronic controller is an electric control unit 118, a crystal clock 120 and appropriate telemetry 122.

Further details relating to the electronic controller and its relationship with the operating components of the delivery device are shown in block diagram form in FIG. 25. More particularly, this figure shows the relative relationship among the fill means of the device, the fluid reservoir, the device gel reservoir, the electrical source, the catheter and a reservoir positioning sensor, the details of which will presently be described. Additionally, FIG. 25 illustrates, in block diagram form, the relationship among these components and the various components that make up the electronics of the device including the central processing unit, the RAM/ROM memory, the digital signal processor, the logic circuit and the telemetry assembly. As previously mentioned, the various electronic components and related systems of the device are well known to those skilled in the art and their interconnection and programming to meet the various requirements of the physician and patient protocol are well within the capability of the skilled artesan.

Upon filling the drug reservoir and after the electronic controller is initially programmed in a manner well understood by those skilled in the art, the device can be implanted into the patient. In the paragraphs that follow, the electronics as well as the method of programming the electronics will be further described.

In one form of the invention, when current flow to electrodes 92a and 92b is stopped by the controller, expandable gel 46 will expand to the configuration shown in FIG. 8. With the apparatus in the configuration shown in FIG. 6, with current flowing to the electrodes, fluid can be introduced into reservoir 36 in the manner previously described via septum 34 so that the apparatus will assume the configuration shown in FIG. 7. Upon interruption of power to electrodes 92a and 92b, the expandable gel will expand into the configuration shown in FIG. 8 causing fluid to be expelled from the device via cannula assembly 42. It should also be understood that other electroresponsive gels can be used which will expand or swell into the configuration shown in FIG. 8 upon power being supplied to the electrodes.

Referring next to FIGS. 19 through 23, another form of the apparatus of the invention is there shown and generally designated by the numeral 130. This embodiment of the invention is similar in many respects to the embodiment shown in FIGS. 1 through 18 and like numerals are used in FIGS. 19 through 23 to identify like components. This latest embodiment is also designed to be implanted into the body of the patient in the manner previously described. As before the apparatus comprises a titanium base or shell 132 and a titanium cover or shell 134 that can be joined together as by welding to form the hollow housing 136 of the device. Unlike the embodiment of the invention shown in FIGS. 1 through 19, here the device uniquely includes integral, interactive physiological sensor means and sensor connecting means for interconnecting the sensor with the device electronics disposed within housing 136.

The delivery device is adapted to be implanted within the patient's body at a location immediately below a layer of skin so that an access port 138 formed in the housing can be accessed by a hypodermic needle to introduce, in the manner previously described, a quantity of liquid medicament such as heparin, morphine, insulin or like medicament through a septum 34 into a drug reservoir. During operation, the medicament is delivered from the delivery device via a cannula port 40 to which a cannula assembly 42 is attached.

Housing 136 houses the novel electrically activated stored energy source of the invention which functions to cause the fluids contained within the sealed reservoir of the device, the character of which was previously described, to flow outwardly thereof through an outlet port formed in cover 134. As in the earlier described embodiments, the electrically activated means or stored energy source, is provided in the form of an electroresponsive gel which is disposed within an expandable, hermetically sealed metal bellows assembly that is of the character previously described. The expandable or swellable mass is also of the same character as previously described herein. A carrier assembly 54 having an electronics receiving channel 56 supports an annular shaped PC board 58 (FIG. 23) and the electronic components associated therewith, the character of which are shown in FIG. 17 and which have previously been described.

Connected to and extending from cover 134 is the previously identified sensor means of the invention, for sensing various body conditions. The sensor means, which may comprise commercially available chemical, electrochemical, and optical type sensors, here includes a connector 140, a conduit 142 and a sensor 144. Connector 140 includes a ribbed body portion 140a that is sealably receivable within a threaded receiving opening 146 formed in a protuberance that extends from the periphery of housing 136 in the manner shown in FIGS. 22 and 23. Conduit 142 extends through connector 140 and includes connector leads 140b that are connected to PC board 58 in the manner best seen in FIG. 23. A threaded connector 152, which is threadably received within threaded receiving opening 154 formed in protuberance 148, maintains sensor connector 140 securely in position. The sensor tip 144 is appropriately positioned within the patient at the time of implantation of the delivery device.

Figure 24:
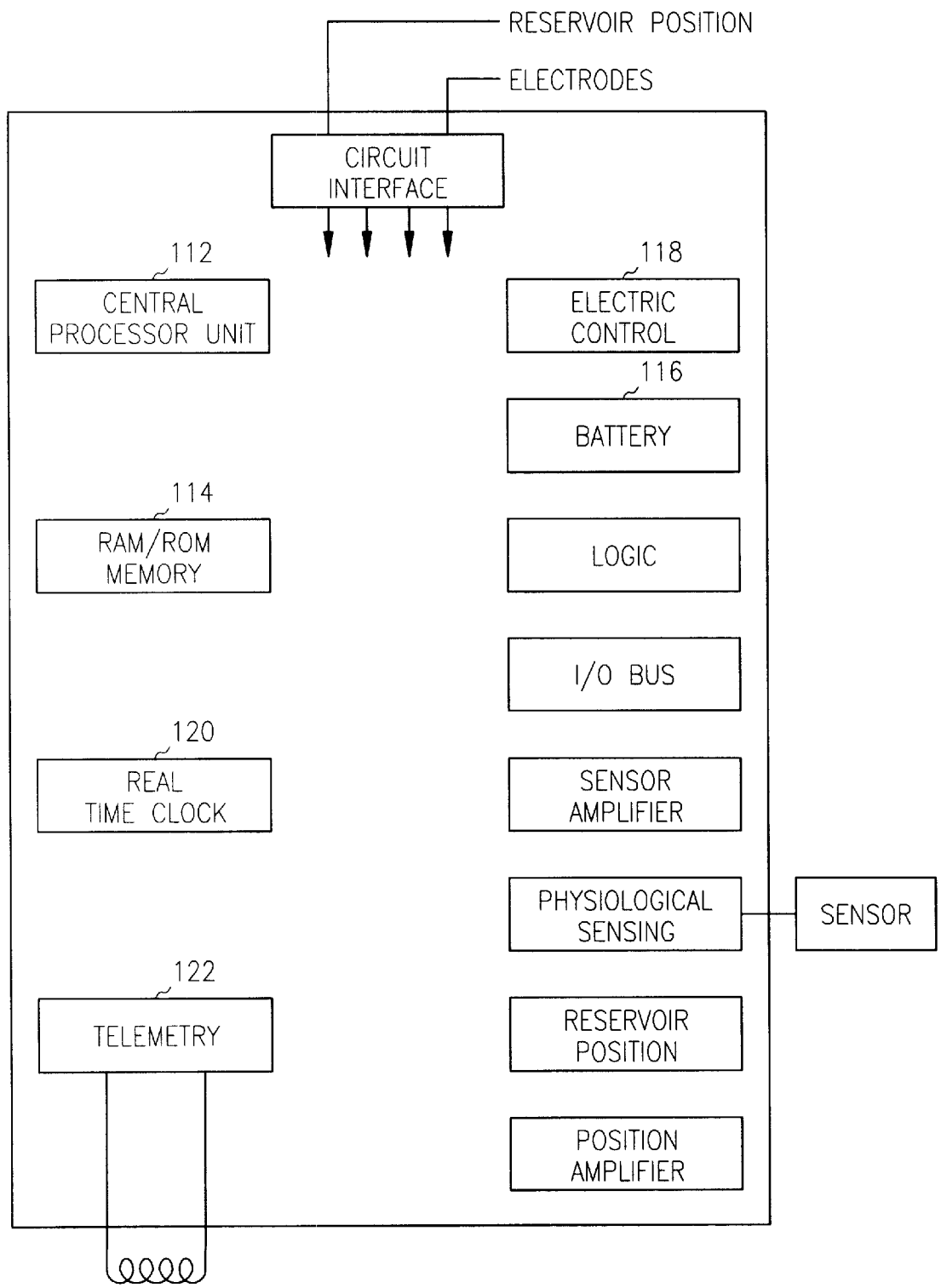
FIG. 24 is a generally diagrammatic view showing the relationship among the various components of the central control unit and stimulation means of the embodiment shown in FIG. 19.

As indicated in FIGS. 24 and 25, this latest embodiment of the invention uniquely comprises an In vivo, physiological sensing portion generally designated as 147 that is capable of detecting and responding to the physiological, physiochemical, chemical, optical and electronic changes in the body or bloodstream. The physiological sensing portion and its sensing structure may comprise an electronic, chemical or optical interface designed to measure specific parameters or changes in parameters and to compare known values combined within the associated delivery system electronic memory. It will be clear to those skilled in the art that, when the physiological sensing portion 147 is coupled directly or indirectly with a sensing amplifier 149 (FIG. 25), with related filter 151, analog to digital converter 153, signal processor 155 and other sensing circuitry operating in conjunction with the programmable system electronics/CPU that various physiological or chemical changes may be sampled and compared with known parameters set forth in a look-up table carried in device memory.

When necessary the CPU/electronic controller 157 can be programmed to execute a command function signal to initiate control and/or terminate the timed operation and frequency of current flow. The resulting process is responsive to the physiological/chemical sensor circuitry and the output can be converted to digital signals and referenced against other controlling data will provide the interactive operating mode of operation of the delivery system.

Other suitably installed sensors which can measure bellows position location and displacement and related sensing circuitry, which comprise a part of the electronics of the apparatus, will also provide various signals including on/off function feedback signals for associated pulse logic sequences. Additionally, drug volume displacement, delivery rate over time measurements, battery life and system temperature and like data can be provided. Other alarm data can also be provided as, for example, reservoir condition and component malfunction. The telemetry assembly relies on the use of a radio frequency transmission system that can readily be adapted from commercially available systems that are well known to those skilled in the art. With the use of such a system, it is possible to up link the system performance, event history data residing in the receiving register and other operating parameters and current values such as the remaining drug volume and battery life.

Further the telemetry assembly can receive down link instructions upon proper interrogation and address confirmation in the programmable system operating mode. Such programming changes of function and operating values can be implemented and recorded within the delivery system electronics controller memory. This program can also be accomplished through the use of an operably associated portable system programmer and programming head which also can be readily adapted from commercially available systems that are well known to those skilled in the art.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A device for infusing medicinal fluid into a patient at a controlled rate comprising:
   (a) a housing having an outlet;
   (b) a fluid reservoir containing a fluid disposed within said housing, said fluid reservoir having an inlet and an outlet in communication with said outlet of said housing;
   (c) an expandable mass disposed within said housing proximate said reservoir, said expandable mass comprising a semi-solid, which will respond to a change in electric field in a manner to act upon said fluid within said reservoir to cause said fluid to flow outwardly of said outlet of said reservoir; and
   (d) control means operably associated with said expandable mass for changing the electric field acting upon said expandable mass.

2. The device as defined in claim 1 in which said mass is disposed within a first expandable structure disposed within said housing.

3. The device as defined in claim 1 further including means for forming said reservoir said means comprising a second expandable structure disposed within said housing and operably associated with said first expandable bellows.

4. The device as defined in claim 1 in which said mass comprises a electroresponsive gel.

5. The device as defined in claim 1 further including a cannula connected to said housing and communicating with said reservoir for delivering fluid from said reservoir to the patient.

6. The device as defined in claim 1 further including an ullage disposed within said housing and located proximate said fluid reservoir.

7. The device as defined in claim 1 in which said mass expands upon a change in the electric field acting upon said mass.

8. The device as defined in claim 1 in which said mass contracts upon a change in the electric field acting upon said expandable mass.

9. The device as defined in claim 1 further including fill means in communication with said reservoir for filling said reservoir.

10. The device as defined in claim 9 in which said housing comprises a base and a cover superimposed over said base and in which said fill means comprises a septum disposed within said cover, said septum being pierceable by a cannula inserted into said septum.

11. An implantable device for implantation within a patient for infusing medicinal fluid into the patient at a controlled rate comprising:
    (a) a housing having an outlet;
    (b) a fluid reservoir containing a fluid disposed within said housing, said reservoir having an inlet and an outlet in communication with said outlet of said housing;
    (c) an electroresponsive, expandable polymer gel disposed within said housing proximate said reservoir, said polymer gel upon being stimulated by electric current, will expand so as to act upon said fluid within said reservoir to cause said fluid to flow outwardly of said outlet of said reservoir; and
    (d) stimulation means for stimulating said polymer gel, said stimulation means comprising a source of electric current.

12. The device as defined in claim 11 in which said polymer gel is contained within an expandable structure disposed within said housing.

13. The device as defined in claim 11 further including a second expandable structure disposed within said housing, said fluid reservoir being formed by said second expandable structure.

14. The device as defined in claim 11 in which source of electric current comprises an electric circuit.

15. The device as defined in claim 11 in which said source of electric current comprises:
    (a) a base;
    (b) a pair of spaced-apart electrodes connected to said plate; and
    (c) a source of electricity connected to said electrodes.

16. The device as defined in claim 11 further including an impedance frit disposed between said fluid reservoir and said outlet of said housing.

17. The device as defined in claim 11 further including a delivery cannula connected to said outlet of said housing for delivery fluid to the patient.

18. The device as defined in claim 10 further including sensor means connected to said housing for sensing changes in the patient's body.

19. The device as defined in claim 11 further including fill means carried by said housing for filling said reservoir.

20. The device as defined in claim 19 in which said fill means comprises a septum carried by said housing, said septum being pierceable by a cannula inserted into said septum.

21. An implantable device for implantation within a patient for infusing medicinal fluid into the patient at a controlled rate comprising:
    (a) a housing having an outlet;
    (b) a fluid reservoir containing a fluid disposed within said housing, said reservoir having an inlet and an outlet in communication with said outlet of said housing;
    (c) an electroresponsive, expandable polymer disposed within said housing proximate said reservoir, said polymer, upon being stimulated, expanding to act upon said fluid within said reservoir to cause said fluid to flow outwardly of said outlet of said reservoir;
    (d) stimulation means for stimulating said expandable polymer, said stimulation means comprising a source of electrical current; and
    (e) delivery means connected to said outlet of said housing for delivering fluid to the patient.

22. The device as defined in claim 21 in which said polymer gel undergoes a change in polymer conformation upon being stimulated.

23. The delivery devices defined in claim 21 in which said delivery means comprises an elongated cannula having a first end connected to said outlet of said housing and a second end terminating in a porous tip.

24. The device as defined in claim 21 in which said expandable polymer is contained within an expandable structure disposed within said housing.

25. The device as defined in claim 21 further including a second expandable structure disposed within said housing, said fluid reservoir being formed by said second expandable structure.

26. The device as defined in claim 21 further including physiological sensor means connected to said housing for sensing physiological changes in the patient.

27. The device as defined in claim 21 further including fill means carried by said housing for filling said reservoir.

28. The device as defined in claim 27 in which said fill means comprises a septum carried by said housing, said septum being pierceable by a cannula inserted into said septum.

* * * * *